United States Patent [19]

Komura

[11] Patent Number: 4,548,373

[45] Date of Patent: Oct. 22, 1985

[54] MEDICAL EQUIPMENT SUPPORTING DEVICE

[75] Inventor: Seiichi Komura, Osaka, Japan

[73] Assignee: Tokyo Kogaku Kikai Kabushiki Kaisha, Tokyo, Japan

[21] Appl. No.: 589,273

[22] Filed: Mar. 12, 1984

[30] Foreign Application Priority Data

Mar. 22, 1983 [JP] Japan ............................. 58-39583[U]
Feb. 20, 1984 [JP] Japan ............................. 59-23355[U]

[51] Int. Cl.[4] ............................................. B61L 13/00
[52] U.S. Cl. .................................. 248/122; 248/280.1; 188/171; 188/72.9
[58] Field of Search ............... 248/324, 122, 123.1, 248/124, 125, 292.1, 280.1; 188/173, 171, 72.9

[56] References Cited

U.S. PATENT DOCUMENTS

| | | | |
|---|---|---|---|
| 3,003,589 | 10/1961 | Desbrow | 188/72.9 |
| 3,221,845 | 12/1965 | Hansen | 188/171 |
| 3,795,290 | 3/1974 | Hori | 188/171 |
| 4,166,602 | 9/1979 | Nilsen | 248/324 |
| 4,181,201 | 1/1980 | McCarthy | 188/171 |
| 4,185,801 | 1/1980 | Plymoth | 248/122 |
| 4,344,595 | 8/1982 | Heller | 248/280.1 |
| 4,364,535 | 12/1982 | Itoh | 248/280.1 |
| 4,397,439 | 8/1983 | Wilbur | 248/280.1 |

Primary Examiner—Reinaldo P. Machado
Assistant Examiner—Alvin Chin-Shue
Attorney, Agent, or Firm—Browdy and Neimark

[57] ABSTRACT

Disclosed herein is a medical equipment supporting device comprising a support pole and a polyarticulated arm supported by said support pole and adapted to support a medical equipment by said polyarticulated arm, characterized in that a brake disc is fitted in a rotary shaft of at least one of joints of the polyarticulated arm, and inside of an arm element of the polyarticulated arm are provided brake shoes for holding said brake disc therebetween in a pressed manner, means for ordinarily exerting a holding force on the brake shoes, and means for releasing the brake disc from the holding force of the brake shoes in response to an instruction signal from an instruction means to be operated by an operator.

4 Claims, 3 Drawing Figures

MEDICAL EQUIPMENT SUPPORTING DEVICE

BACKGROUND OF THE INVENTION (1) Field of the Invention

The present invention relates to a device for supporting a medical equipment such as an operation microscope, a surgeon's knife using laser beam (laser mes), an X-ray machine, etc., and more particularly, it relates to a braking system of a polyarticulated arm adapted for supporting the medical equipment at one end thereof and attached to a support pole of the supporting device at the other end while being designed to be rotatable or pivotable.

(2) Description of the Prior Art

In the medical equipment such as the operation microscope, the laser mes, the X-ray machine and the like which are used to treat, examine or insepct diseased portions by optical or electronic means, it is necessary to locate the equipment at a place where the diseased portions are conveniently or best observed and the treatment or operation is not interrupted by the equipment. For this purpose, there have been already put into practical use the medical equipment supporting devices which can support the medical equipment at an arbitrary spatial position by the construction that the polyarticulated arm is rotatably and pivotably supported at one end thereof on a support pole of a floor stand type or a ceiling suspension type, and the medical equipment is attached to the other end of the polyarticulated arm.

In the conventional supporting devices of this type, an arm rotary shaft at each joint of the polyarticulated arm is clamped by means of a locking screw so that the medical equipment may be fixed at an arbitrary spatial position. Thus, when a number of the joints of the polyarticulated arm is increased to assure a large latitude in movement and enable fine adjustment, the number of the locking screws are proportionally increased. Consequently, the operation becomes extremely troublesome because a number of these locking screws must be loosened or tightened every time the medical equipment is intended or required to be moved to another spatial position. Particularly, since the operation microscope, for instance, the operation microscope for use in neuro surgery or otorhinolaryngological surgery is required to be frequently adjusted in the spatial position during operation because the diseased portions undergoing the operation are extended over a relatively wide range in three dimension and the observation must be made in an extremely many directions. Further, in case an operator moves the microscope, the locking screws must always be maintained in a sterilized state, which is a very hard task. If the locking screws are not sterilized, the operator or his operation assistant is not allowed to touch them and another person's help is necessary for moving the microscope.

As an example of the prior art eliminating the above drawbacks, there is a supporting device disclosed in Japanese Patent Application Laid Open No. 48-40450. According to this supporting device, the polyarticulated arm is prevented to be rotatively moved by supplying a current to an electromagnet installed in each joint portion of the polyarticulated arm (three-dimensionally adjustable Carden link mechanism), and the arm comes to be rotatively moved by cutting off the electric power supply to the electromagnet through the operators switching-off action, whereby the medical equipment can be moved and stopped at a desired spatial position. Since this supporting device uses the electromagnet to restrain the rotative movement of the polyarticulated arm, the supporting device itself becomes not only expensive, but also running cost rises because the electromagnet must continue to be energized to fixedly support the medical equipment, except when the medical equipment is moved.

SUMMARY OF THE INVENTION

It is therefore an object of the present invention to provide a novel medical equipment supporting device which eliminates the drawbacks possessed by the conventional medical equipment supporting devices.

Another object of the invention is to provide a medical equipment supporting device equipped with means for restraining the rotative movement of a polyarticulated arm, which is simple in structure and is cheap in manufacturing cost as well as running cost.

In order to accomplish the above-mentioned objects, the medical equipment supporting device according to the invention is constituted by the construction that a brake disc is provided at a rotary shaft at least one joints of the polyarticulated arm, and inside of an arm member are provided brake shoes adapted to hold the brake disc therebetween in a pressed manner, a pressure-exerting means adapted for always exerting the holding pressure upon the braking shoes, release means adapted for releasing the brake disc from the pressure exertion of the brake shoes thereupon against the pressure of the pressure-exerting means in response to an instruction signal from an instruction means to be operated by the operator.

According to another aspect of the invention, the medical equipment supporting device is also characterized by the construction of two stage adjustment that the medical equipment is normally fixedly supported at an arbitrary spatial position by the holding pressure given by the pressure-exerting means; and when the spatial position of the medical equipment is intended to be slightly or finely adjusted, the polyarticulated arm is moved by a force overcoming the holding pressure, while when the release means is actuated to release the brake disc from the holding pressure, the medical equipment can be moved over a wide range by a small force.

In the medical equipment supporting device according to the invention thus constructed, it is no need to perform a troublesome operation of tightening or loosing the locking screws as in the case with the conventional supporting devices, and the supporting device itself is cheap not only in manufacturing cost but also in running cost since the braking mechanism is of an extremely simple mechanical system.

These and other objects, features and advantages of the invention will be well appreciated upon reading of the following description of the invention when considered in conjunction with the attached drawings with understanding that some modifications, variations, and changes could be easily made by the skilled in the art to which the invention pertains without departing from the spirit of the invention and the scope of the claims appended hereto.

BRIEF DESCRIPTION OF THE ATTACHED DRAWINGS

DETAILED DESCRIPTION OF THE PREFERRED EMBODIMENTS

Figure 1:
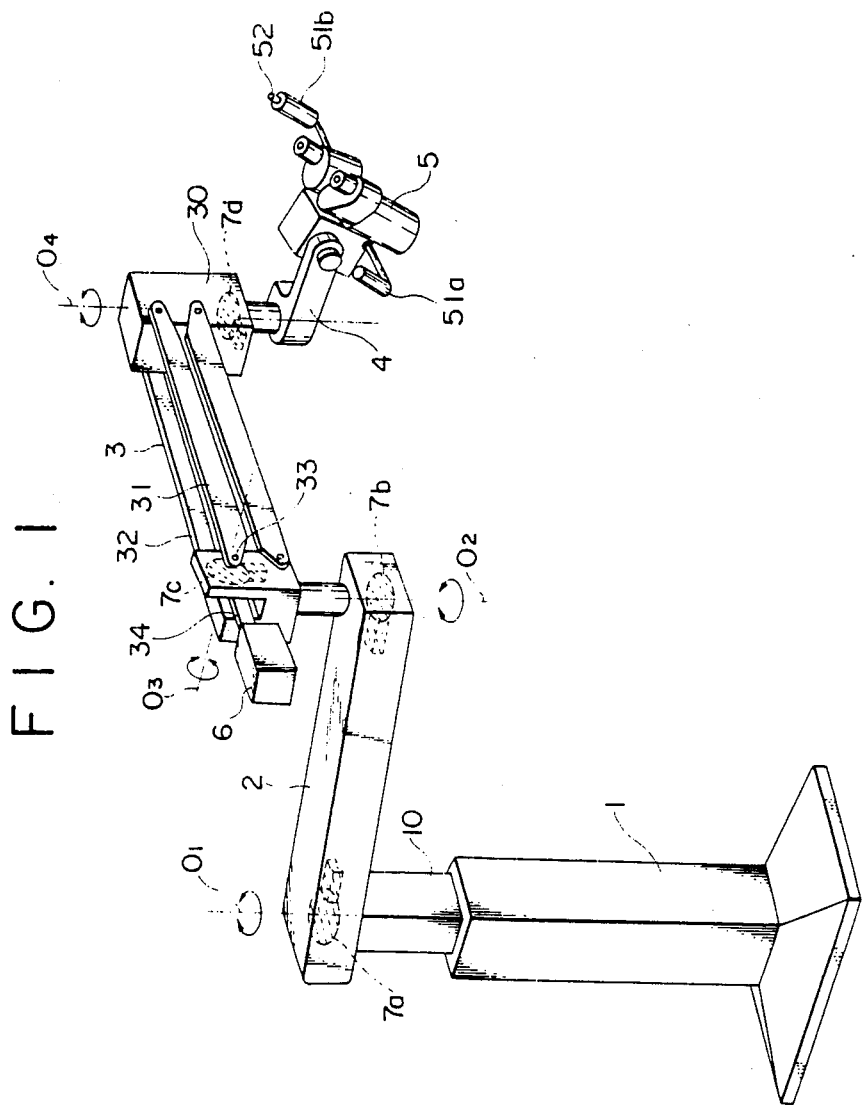
FIG. 1 is a perspective view illustrating the exterior of a first embodiment of a medical equipment supporting device according to the invention.

In the following, the present invention will be described more in detail with reference to the embodiments shown in the drawings.

Figure 2:
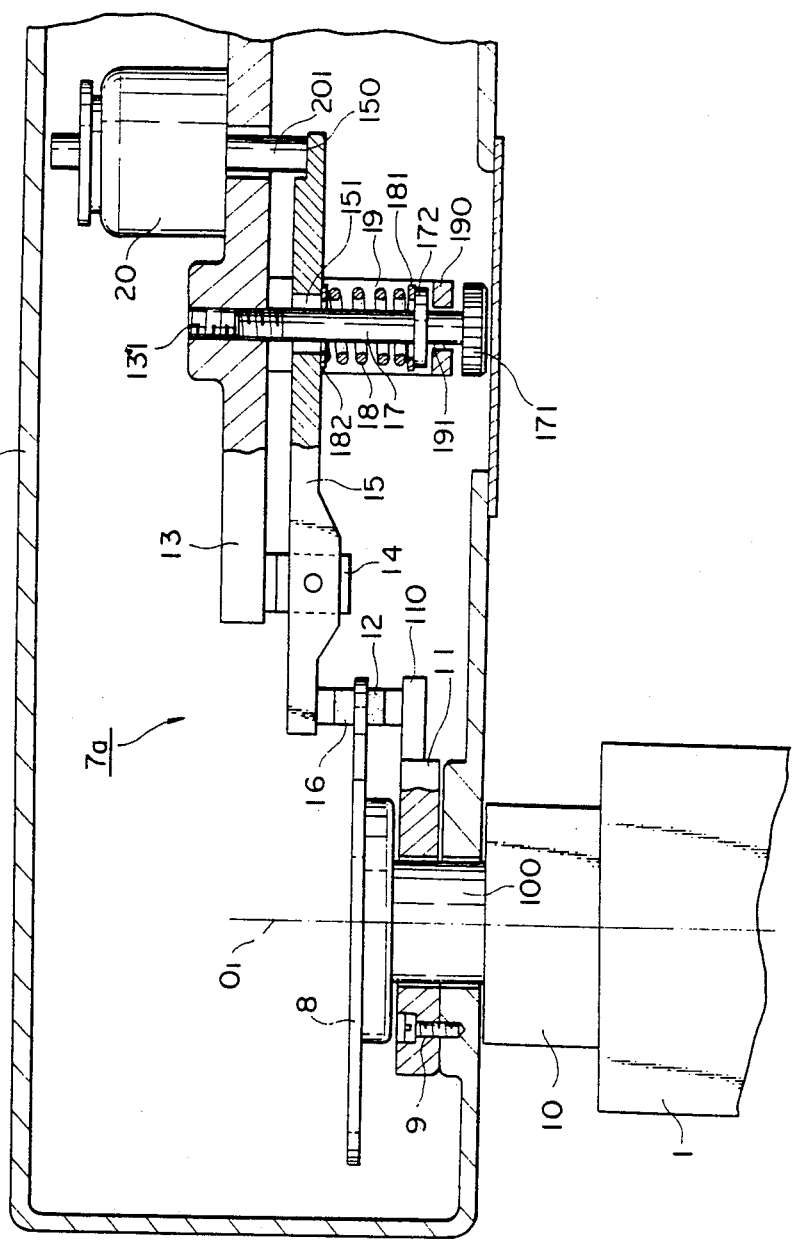
FIG. 2 is a vertical view partially in section of a first arm member shown in FIG. 1.

FIGS. 1 and 2 illustrate a first embodiment according to the invention, FIG. 1 being a perspective view of the exterior of the medical equipment supporting device in the state that an operation microscope is supported. In this figure, a reference numeral 1 is a stand to be placed on a floor of an operating room, and a support pole 10 is supported inside of this stand 1 to be movable in a vertical direction. To the upper end of the support pole 10 is attached a first arm element 2 to be rotatably supported around a perpendicular axis $O_1$ at one end thereof to be rotatable in a horizontal plane. To the other end of the arm element 2 is attached a second arm element 3 to be rotatable around a perpendicular axis $O_2$, thus constituting a part of a polyarticulated arm. The second arm element 3 constituting a part of the polyarticulated arm is constructed as a parallelogram link mechanism and adapted to be pivotally moved around a horizontal axis $O_3$ as its rotary axis. To the lower side of the tip end portion 30 of the second arm element 3 is attached a microscope arm 4 to be rotatable around a perpendicular axis $O_4$. The microscope arm 4 is equipped with a microscope body 5 at the tip portion thereof. An extention 34 extended in a direction opposite to the direction in which are stretch out link arms 31 and 32 having a link fulcrums 33 on the horizontal rotary axis $O_3$ is provided with a balance weight 6 for balancing the weight of the microscope body 5 hanged from the tip portion 30 of the second arm element 3. Braking means 7a to 7d are installed respectively inside of the arm elements 2, 3 and around the axes $O_1$ to $O_4$ as the rotation or pivot center of the arm elements of the support device.

Since the structure of the braking means are common to one another, explanation will be made with referring to FIG. 2 taking the braking means 7a as an example. A brake disc 8 is attached to the upper end of a rotary shaft 100 formed on the top portion of the support pole 10. A base disc 11 which is integrated with the first arm element 2 by means of a screw 9 to be rotated around the shaft 100 is provided downward of the brake disc 8, and at the arm portion 110 of the base plate 11 is attached a brake shoe 12. Meanwhile, a bearing 14 is attached to the under face of a base plate 13 fixed to and within the arm element 2, and rotatively supports a brake arm 15. At one end of a brake arm 15 is provided a brake shoe 16 in such a position that it can hold the brake disc 8 in a pressed manner in cooperation with the brake shoe 12. Against the other end 150 of the brake arm 15 is abutted the tip portion of a push rod 201 of a solenoid 20 which is attached on the base plate 13.

As shown in FIG. 1, the solenoid 20 is designed to push down the push rod 201 by turning on an instruction switch 52 installed in the tip portion of one of control levers 51a and 51b attached on both sides of the microscope 5. A U-letter shaped guide member 19 is attached to the lower face of the base plate 13. A pressure-adjusting bolt 17 which is equipped with a knob 171 and a collar 172 attached at its lower end and middle portion respectively is inserted into an opening 191 formed in a bar 190 of the guide member 19. The tip portion of the bolt 17 is screwed to a female screw portion 131 formed in the base plate 13 which penetrating an opening 151 formed in the brake arm 15. A spring 18 is interposed between the collar 172 of the bolt 17 and the under face of the brake arm 15 via washers 181 and 182. The spring 18 always urges the brake arm 15 upwardly, so that the brake shoe 16 ordinarily holds the brake disc 8 in the pressed manner in cooperation of the brake shoe 12. Thereby, the arm is restrained from rotating.

The brake shoes 12 and 16 are made of an elastic wearing material such as rubber, and the spring force of the spring 18 is selected such that the microscope body 5 may not be spontaneously moved from the located position.

Next, the operation of the medical equipment supporting device according to the invention will be explained below.

When the microscope body 5 is intended to be finely moved, the operator grasps the control levers 51a and 51b (see FIG. 1) and moves the microscope body 5, so that the arm elements can be rotatively moved finely against the frictional force between the brake disc 8 and the brake shoes 12 and 16. The spring force of the spring 18 can be freely adjusted in such a manner that the knob 171 is turned to displace the bolt 17 in an axial direction thereof, which in turn causes the collar 172 to change its pushing force upon the spring 18.

When the spatial position of the microscope 5 is intended to be largely changed, the instruction switch 52 is turned on to actuate the solenoid 20, which pushes down the push rod 201 against the pushing-up force of the spring 18. Thereby, the brake arm 15 is pivoted downwardly to release the disc brake 8 from the holding force of the brake shoe 16 thereupon, and accordingly the microscope can be moved by a small force. In particular, since this embodiment adopts the paralelogram link mechanism in which the second arm element is equipped with the balance weight 6, the microscope can be very lightly and smoothly moved.

In the embodiment illustrated above, the rotary axis $O_1$ to $O_4$ are installed in the braking means 7a to 7d respectively, but according to the invention, it is not always necessary to install the braking means in all of the rotary shaft.

Especially because the weight of the second arm composed of the link mechanism is well balanced, no braking means may be installed around the horizontal axis $O_3$.

Figure 3:
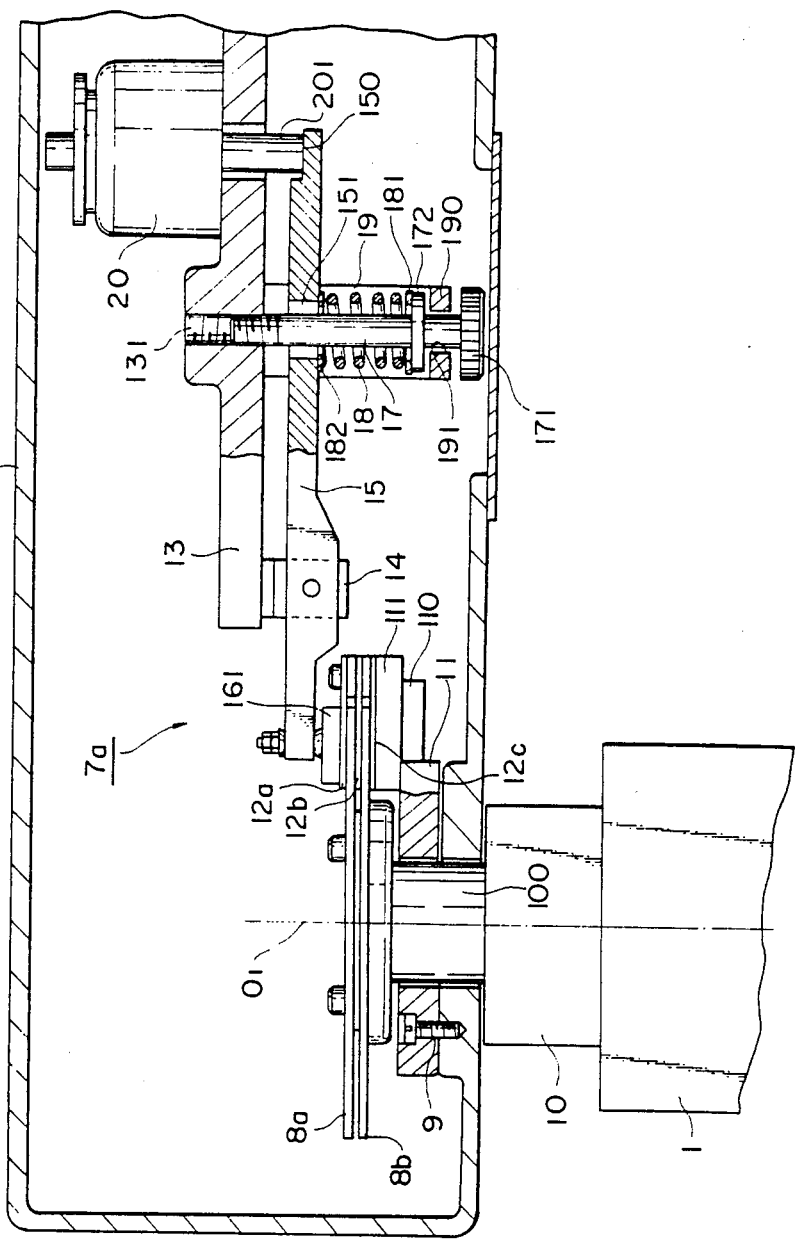
FIG. 3 is a vertical view partially in section of a second embodiment similar to the one in FIG. 2.

FIG. 3 is a view similar to FIG. 2 and illustrating a second embodiment according to the invention. In the embodiment of FIG. 3, although the brake disc, brake shoes, and the pressure-exerting means are different from those of the first embodiment, the other parts are the same as those in FIG. 1. To the rotary shaft 100 are attached brake discs 8a and 8b made of, for instance, stainless steel, which are spaced from one another in an axial direction of the rotary axis at their circumferential edge portions and are opposed to each other. A plurality of brake shoe plates, three steel brake shoe plates 12a, 12b and 12c in this embodiment are fitted on the arm portion 110 of the base disc 11 via a base seat 111. The brake shoe plates 12a, 12b and 12c are spaced from and opposed to one another, and extended at such an area that they may face the circumferential edge portions of the brake discs 8a and 8b while being adapted for holding the both faces of the discs therebetween. A brake shoe-pressing member 161 is provided at one end of the brake arm 15 in such a position that the pressing plate 161 may hold in a pressed manner the brake shoe plates 12a, 12b and 12c and the brake discs 8a and 8b in cooperation with the base seat 111. Therefore, the large frictional force can be assured in an ordinary state because the brake disc 8a and 8b are in plane contact with the brake shoe plates 12a, 12b and 12c, and accordingly the arm is prevented from being rotated by a small holding force. A smaller spring force of the spring 18 may be selected such that the microscope body 5 may not be moved spontaneously from the located position. Since the frictional contact area becomes larger, a range in which the spring force of the spring 18 can be positioned becomes larger as compared with the conventional supporting device. The operation of the supporting device in FIG. 2 is the same in the first embodiment except that the brake discs 8a and 8b can be fixedly held from their both faces by a smaller holding force by means of the brake shoe plates 12a, 12b and 12c to prevent the rotative movement of the polyarticulated arm.

As mentioned above, according to the invention, the operationability is excellent because it is possible to easily locate the medical equipment while handling the control levers and operating the medical equipment, and the structure is simple with cheap manufacturing and running costs. Further, according to the medical equipment supporting device of the invention, the polyarticulated arm can be prevented from rotating or pivoting by a small force, while the fine adjustment in position can also be easily done.

What is claimed is:

1. A medical equipment supporting device comprising:

a support pole having a shaft;

an arm rotatably supported by said shaft at one end thereof, said arm supporting medical equipment at the other end thereof;

at least one brake disc fitted on said shaft;

brake shoes fitted on the inside of said arm for holding said at least one brake disc therebetween in pressed manner;

leveraged brake shoe-pressing means for ordinarily exerting a holding force on one of said brake shoes; and release means for releasing said brake shoes from the holding force of said brake shoe-pressing means in response to an instruction signal from instruction means to be operated by an operator;

the holding force of said brake shoe-pressing means being selected such that it fixedly supports said arm relative to said support pole when said arm is at rest, whereby when said arm is moved relative to said support pole without operating said instruction means, said brake shoes can be moved on said at least one brake disc against the holding force of said brake shoe-pressing means to enable said arm to be finely adjusted in position, and when said arm is moved upon operating said instruction means, said brake shoes are released from the holding force of said brake shoe-pressing means, but are maintained in sufficient friction contact with said at least one brake disc to prevent spontaneous rotation of said arm relative to said support pole shaft due to the weight of the arm itself and its distribution about the shaft.

2. The medical equipment suppporting device according to claim 1, wherein said at least one brake disc comprises a plurality of brake disc members which are spaced from one another in an axial direction of said shaft at circumferential edge portions thereof and which are disposed opposite each other, and said brake shoes comprise a plurality of brake shoe plates which are radially extended for facing the circumferential edge portions of said brake disc members and which hold said brake disc members by upper and lower faces thereof.

3. The medical equipment supporting device according to claim 1, wherein said brake shoe-pressing means comprises a brake arm which is pivotally supported about a fulcrum disposed within said arm, said brake shoe-pressing member being fitted on one end of said brake arm for engaging with one outer face of said brake shoe plates, and spring means bearing against said brake arm at a position between said fulcrum and the opposing end of said brake arm for ordinarily exerting the holding force upon said brake shoe plates;

wherein said release means comprises solenoid means actuated in response to an instruction from said instruction means, and a push rod carried by said solenoid means which is engagable with said opposing end of said brake arm when said solenoid is activated.

4. The medical equipment supporting device according to claim 1, wherein said arm is a polyarticulated arm composed of a plurality of arm elements each being rotatably supported relative to another.

* * * * *